United States Patent
Atsumi et al.

(10) Patent No.: US 7,713,393 B2
(45) Date of Patent: May 11, 2010

(54) GAS SENSOR AND METHOD FOR MANUFACTURING THE SAME

(75) Inventors: Takayoshi Atsumi, Kounan (JP); Hiroshi Isomura, Nagoya (JP); Keita Nakagawa, Kakamigahara (JP); Toru Furuichi, Kounan (JP); Takao Kojima, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1118 days.

(21) Appl. No.: 11/185,681

(22) Filed: Jul. 21, 2005

(65) Prior Publication Data

US 2006/0024202 A1 Feb. 2, 2006

(30) Foreign Application Priority Data

Jul. 22, 2004 (JP) ............................. 2004-214907
Jun. 30, 2005 (JP) ............................. 2005-193184

(51) Int. Cl.
*G01N 27/407* (2006.01)

(52) U.S. Cl. .................... 204/429; 204/428; 205/784.5; 73/23.31; 73/23.32

(58) Field of Classification Search ......... 204/424–429; 205/783.5–785, 781; 73/23.31–23.32
See application file for complete search history.

(56) References Cited

U.S. PATENT DOCUMENTS

| 4,863,583 | A | | 9/1989 | Kurachi et al. |
| 5,271,821 | A | | 12/1993 | Ogasawara et al. |
| 5,443,711 | A | | 8/1995 | Kojima et al. |
| 5,733,504 | A | * | 3/1998 | Paulus et al. .................. 422/83 |
| 6,210,552 | B1 | * | 4/2001 | Mizutani et al. ............ 204/429 |
| 6,210,641 | B1 | | 4/2001 | Yamada et al. |
| 6,672,137 | B1 | | 1/2004 | Isomura et al. |

FOREIGN PATENT DOCUMENTS

| EP | 0 267 765 A2 | 5/1988 |
| EP | 0 372 425 A2 | 6/1990 |
| EP | 1 195 601 A2 | 4/2002 |
| EP | 1 321 765 A2 | 6/2003 |
| JP | 1-203963 | 8/1989 |
| JP | 5-066214 A | 3/1993 |
| JP | 9-113480 A | 5/1997 |
| JP | 11-237361 | 8/1999 |
| JP | 2000-121597 A | 4/2000 |

\* cited by examiner

*Primary Examiner*—Nam X Nguyen
*Assistant Examiner*—Bach T Dinh
(74) *Attorney, Agent, or Firm*—Sughrue Mion, PLLC

(57) ABSTRACT

A gas sensor having a gas sensor element which includes: a reference electrode; a solid electrolyte layer having oxygen ion conductivity; a detection electrode; and an electrode-protecting layer covering the detection electrode. The electrode-protecting layer is a porous body carrying catalytic metal, and includes: a detection electrode side portion having a catalytic metal loading ratio of more than 0% by weight and not more than 0.005% by weight; and a surface side portion provided closer to the outer surface of the electrode-protecting layer than the detection electrode side portion, the surface side portion having a catalytic metal loading ratio of 0.01% by weight or more.

7 Claims, 6 Drawing Sheets

GAS SENSOR AND METHOD FOR MANUFACTURING THE SAME

BACKGROUND OF THE INVENTION

1. Field of the Invention

This invention relates to a gas sensor adapted for combustion control or the like of an internal combustion engine, and to a method for manufacturing the gas sensor.

2. Description of the Related Art

Gas sensors disposed in the exhaust system of an internal combustion engine for detecting oxygen concentration in exhaust gas are utilized for combustion control of an internal combustion engine. Specifically, a known gas sensor element included in the gas sensor is equipped with: a solid electrolyte layer made of a ceramic such as zirconia having oxygen ion conductivity; a detection electrode disposed on one surface of the solid electrolyte layer and made of platinum or the like for contacting a gas to be measured; and a reference electrode disposed on the other surface of the solid electrolyte layer and made of platinum or the like for contacting a reference gas. On the surface of the detection electrode, moreover, a porous electrode-protecting layer made of alumina-magnesia-spinel or the like is formed to prevent poisoning of the detection electrode.

This gas sensor is a so-called "oxygen-concentration electromotive force type" gas sensor which generates an electromotive force in accordance with the oxygen concentration in the gas to be measured.

There is a need for a gas sensor which more precisely controls combustion of, an internal combustion engine so as to comply with recent, more stringent regulations on exhaust gas. A gas sensor element which satisfies this need must exhibit less deviation in $\lambda$ point from a theoretical one and must precisely measure oxygen concentration. In a conventional gas sensor, however, the measurement precision of oxygen concentration may be impaired depending on the kind or the like of the exhaust gas. For example, hydrogen present in the exhaust gas has a high diffusion rate (the rate at which the exhaust gas reaches the detection electrode through the electrode-protecting layer) and can reach the detection electrode more easily than other components in the exhaust gas. The first diffusing hydrogen reacts with the detection electrode, and the detection electrode may mistakenly determine $\lambda$ point which has deviated from the theoretical one to make precise combustion control difficult.

In order to provide a gas sensor having a small $\lambda$ point deviation and which is capable of controlling precise combustion of the internal combustion engine, JP-A-11-237361 proposes a gas sensor having a catalyst layer containing a catalytic Pt metal or the like which exhibits excellent catalytic performance while covering the electrode-protecting layer. As a result, the hydrogen in the exhaust gas reacts with the catalyst layer to suppress diffusion of hydrogen to the detection electrode, to thereby provide a gas sensor which can reduce $\lambda$ point deviation and which can precisely control combustion of the internal combustion engine.

Also known is a gas sensor (as proposed in JP-A-8-7177) having a catalyst layer containing catalytic metal which covers a catalytic metal-containing electrode-protecting layer. In this gas sensor, more catalytic metal is present in the catalyst layer than in the electrode-protecting layer, so that the hydrogen reacts in the catalyst layer (as disclosed in JP-A-11-237361). Thus, diffusion of hydrogen to the detection electrode can be suppressed so as to reduce $\lambda$ point deviation and thereby provide a gas sensor which can precisely control combustion of the internal combustion engine.

3. Problems to be Solved by the Invention

However, the catalyst layer of JP-A-8-7177 is generally formed by preparing a slurry containing a material for forming the catalyst layer and by applying the slurry to cover the electrode-protecting layer. Therefore, the catalyst layer is not chemically bonded to the electrode-protecting layer, and may peel off of the electrode-protecting layer. The electrode-protecting layer is then directly exposed to exhaust gas containing hydrogen. The fast diffusing hydrogen may contact the detection electrode so as to introduce a deviation error into the intrinsically detected $\lambda$ point and thus make precise combustion control difficult.

According to JP-A-8-7177 similar to JP-A-11-237361, on the other hand, even if the catalyst layer peels off of the electrode-protecting layer, the electrode-protecting layer itself contains catalytic metal. As a result, the catalytic metal in the electrode-protecting layer can react with the hydrogen to suppress diffusion of hydrogen to the detection electrode. Generally, the electrode-protecting layer is formed to cover the detection electrode by a plasma-spray coating so that contact is more intimate therebetween than between the electrode-protecting layer and the catalyst layer.

However, the unburned contents (e.g., CO or the like) in the exhaust gas may be adsorbed by or may react with the catalytic metal carried by the electrode-protecting layer, and the catalytic metal may expand. When the catalytic metal is dispersed in and carried by the electrode-protecting layer, the catalytic metal in the electrode-protecting layer near the detection electrode side may expand and peel off of the detection electrode. The detection electrode is then directly exposed to exhaust gas containing hydrogen. As a result, the presence of hydrogen can introduce a deviation of the $\lambda$ point detected by the defection electrode from the theoretical one and thus make precise combustion control difficult.

SUMMARY OF THE INVENTION

The present invention has been conceived in view of the above-noted problems of the prior art, and an object thereof is to provide a gas sensor which can finely control combustion by reducing deviation in $\lambda$ point and which suppresses peeling of an electrode-protecting layer.

In accordance with a first aspect, the above object of the invention has been achieved by providing a gas sensor comprising a gas sensor element including: a reference electrode for contacting a reference gas; a solid electrolyte layer having oxygen ion conductivity; a detection electrode for contacting a gas to be measured; and an electrode-protecting layer covering the detection electrode. The electrode-protecting layer comprises a porous body carrying a catalytic metal. The electrode-protecting layer includes a detection electrode side portion having a catalytic metal loading ratio of 0.005% by weight or less (but not including 0), and a surface side portion arranged closer to the outer surface of the electrode-protecting layer than the detection electrode side and having a catalytic metal loading ratio of 0.01% by weight or more.

Thus, the electrode-protecting layer carrying the catalytic metal can be directly exposed to the exhaust gas without having to provide a separate catalyst layer on the electrode-protecting layer. In other words, the catalytic metal carried in the electrode-protecting layer can prevent hydrogen from diffusing to the detection electrode so as to reduce the deviation in $\lambda$ point As a result, a gas sensor capable of precisely controlling combustion of the internal combustion engine can be obtained.

In the invention, moreover, the electrode-protecting layer includes a surface side portion having a catalytic metal loading ratio of 0.01% by weight or more. As a result, hydrogen in the exhaust gas can sufficiently react on the surface side portion of the electrode-protecting layer to reduce the deviation in X point, to thereby provide a gas sensor capable of precisely controlling combustion of the internal combustion engine.

In the invention, moreover, the electrode-protecting layer includes a detection electrode side portion having a catalytic metal loading ratio of 0.005% by weight or less (but not including 0). Since the loading ratio of the catalytic metal in the detection electrode side portion of the electrode-protecting layer is smaller than that of the surface side portion, the volume expansion of the catalytic metal caused by adsorption of unburned contents of exhaust gas can be suppressed. As the result, the electrode-protecting layer is less susceptible to peeling.

As used herein the "outer surface of the electrode-protecting layer" means the face of the electrode-protecting layer opposite the face which abuts the detection electrode. Moreover, the "loading ratio of the catalytic metal" means the weight ratio of the catalytic metal incorporated into a predetermined portion of the electrode-protecting layer. The loading ratio is determined as follows. As for the detection electrode side portion, a portion of the electrode-protecting layer in a thickness of up to about 25 μm at the detection electrode side is scraped off. As for the surface side portion, on the other hand, a portion of the electrode-protecting layer having a thickness of about 25 μm, which portion is located closer to the outer surface of the electrode-protecting layer than the detection electrode side portion, is scraped off. Next, the total weight of the individual electrode-protecting layers that are scraped off is measured. Then, the catalytic metal in the detection electrode side portion and in the surface side portion are dissolved in aqua regia, and the weight of the catalyst metal contained therein is measured by an ICP (inductively coupled plasma) luminescence method to thereby determine the respective weight ratios of the catalyst metal at the individual portions to the total.

Moreover, the surface side portion having the above-noted catalytic metal loading ratio may be any portion having a thickness of about 25 μm and located in a position closer to the outer surface of the electrode-protecting layer than the detection electrode side portion The surface side portion may include the outermost surface of the electrode-protecting layer or may be located inside the electrode-protecting layer.

The invention can also be applied either to a gas sensor in the form of a solid electrolyte layer having a bottomed cylinder shape or a laminated type gas sensor having a reference electrode, or to a detection electrode and the like formed on a plate-shaped solid electrolyte layer. Moreover, the electrode-protecting layer may cover at least the detection electrode or the entire surface of the solid electrolyte layer including the detection electrode.

In the invention, moreover, the catalytic metal loading ratio of the catalytic metal of the electrode-protecting layer preferably decreases in the thickness direction from the outer surface side of the electrode-protecting layer to the detection electrode side of the electrode-protecting layer. That is, preferably, a gradient in catalytic metal loading ratio is established in the electrode-protecting layer, where the loading ratio is higher towards the outer surface side than the detection electrode side thereof. On the surface side of the electrode-protecting layer, efficient reaction between the higher loading ratio of catalytic metal can reduce the deviation in λ point to secure precise combustion control. On the other hand, since the loading ratio of the catalytic metal in the electrode-protecting layer gradually decreases moving away from the surface side to the detection electrode side, the stress due to volume expansion of the catalytic metal on the detection electrode side is suppressed so that peeling of the electrode-protecting layer from the detection electrode is likewise suppressed.

As used herein, "the loading ratio of the catalytic metal of the electrode-protecting layer decreases in the thickness direction from the surface side of the electrode-protecting layer to the detection electrode side of the electrode-protecting layer" is verified by scrapping off plural layer portions from the electrode-protecting layer, each having a thickness of about 25 μm, in the thickness direction from the outermost surface; measuring the loading ratio by weight of the catalytic metal in the electrode-protecting layer at the individual portions, and determining that the loading ratio at an inner portion is smaller than that in an outer portion.

The loading amount in the whole electrode-protecting layer of the invention is preferably 10 to 200 μg. When the loading amount is less than 10 μg, the reaction between the electrode-protecting layer and hydrogen may be reduced to result in a difference in diffusion rate of components of the exhaust gas, and the deviation of λ point may make it difficult to precisely control combustion. When the loading amount is more than 200 μg, on the contrary, the diffusion rate of the exhaust gas may be lowered to deteriorate the responsiveness of the gas sensor as a whole. Therefore, a loading amount of 10 to 200 μg in the electrode-protecting layer can reduce the deviation in λ point, to thereby effectively provide a gas sensor exhibiting sufficient responsiveness yet precise combustion control.

The electrode-protecting layer of the invention preferably has a porosity of 5 to 50%. When the porosity is less than 5%, the lowered diffusion rate of the exhaust gas may deteriorate the responsiveness of the gas sensor as a whole. When the porosity is greater than 50%, on the contrary, poor reaction between the electrode-protecting layer and the hydrogen increases the amount of hydrogen diffusing to the detection electrode. Consequently, the resultant deviation in λ point makes precise combustion control difficult. Moreover, responsiveness and durability of the electrode may be easily deteriorated. In a porosity range of 5 to 50%, therefore, the deviation in λ point can be effectively reduced, while maintaining precise combustion control and responsiveness and durability of the electrode.

The electrode-protecting layer of the invention preferably has a thickness of 150 to 500 μm. When the thickness of the electrode-protecting layer is smaller than 150 μm, the reaction between the catalytic metal in the electrode-protecting layer and hydrogen is reduced, and the deviation in λ point may make precise combustion control difficult. When the thickness is greater than 500 μm, on the contrary, the diffusion rate of exhaust gas may be lowered to thereby deteriorate the responsiveness of the gas sensor as a whole, In a thickness range of 150 to 500 μm, therefore, the deviation in λ point can be reduced to effectively provide a gas sensor for precise combustion control.

The porous body of the electrode-protecting layer of the invention preferably contains at least one of alumina, alumina-magnesia-spinel and zirconia. These components are thermally and chemically stable for improving resistance of the electrode-protecting layer to deterioration.

The catalytic metal of the invention is preferably selected from at least one of Pt, Pd, Rh and. Ru. These materials have excellent catalytic performance so that the effects of the invention can be sufficiently secured.

The gas sensor element preferably has a porous poison preventing layer covering the electrode-protecting layer so as to prevent the catalytic metal from becoming poisoned. Thus, even if the electrode-protecting layer is directly exposed to exhaust gas, the catalytic metal carried in the electrode-protecting layer is protected from poisonous substances such as lead, phosphor or silicon in the exhaust gas. As a result, the reaction between hydrogen in the exhaust gas and the catalytic metal is maintained to suppress diffusion of hydrogen to the detection electrode. As a result, the deviation in λ point can be reduced to provide a gas sensor which can precisely control combustion of the internal combustion engine.

Moreover, the poison preventing layer of the invention preferably contains titania and a ceramic other than titania Among ceramic materials, titania is effective in adsorbing poisonous substances, and the poison preventing layer containing titania can react effectively with poisonous substances such as phosphor or the like in the exhaust gas, to thereby prevent the catalytic metal in the detection electrode and in the electrode-protecting layer from becoming poisoned. The ceramic other than titania is preferably exemplified by ceramic materials resistant to thermal shrinkage, such as spinel or mullite. Such ceramic materials improve the durability of the poison preventing layer, which exhibit high endurance against peeling from the electrode-protecting layer due to thermal shrinkage.

Moreover, the poison preventing layer is preferably formed from titania powder having a peak particle size distribution of primary particles of 1 μm or less, and from ceramic powder other than titania powder having a peak particle size distribution of primary particles of 10 μm or more. By thus adjusting the particle size distribution of the primary particles of the titania powder and the ceramic powder other than titania in the material for the poison preventing layer, good air permeability of the poison preventing layer is maintained, and poisonous substances are adsorbed without difficulty.

According to another aspect, the present invention provides a method for manufacturing a gas sensor having a gas sensor element including, in the following order: a reference electrode for contacting a reference gas; a solid electrolyte layer having oxygen ion conductivity; a detection electrode for contacting a gas to be measured; and an electrode-protecting layer covering the detection electrode, the electrode-protecting layer comprising a porous body carrying a catalytic metal. The manufacturing method comprises: spray coating a porous body on detection electrode; impregnating the porous body with a catalytic metal from its outer surface; and heating the porous body impregnated with the catalytic metal to form the electrode-protecting layer.

The porous body thus formed by spray coating is impregnated with a catalytic metal from the outer surface thereof so that the loading ratio of the catalytic metal in a surface side portion of the electrode-protecting layer can be controlled to be greater than that in a detection electrode side portion of the electrode-protecting layer. The surface side portion can be formed at least in the outermost surface of the electrode-protecting layer. As a result, hydrogen in the exhaust gas can react sufficiently at the surface side portion to suppress diffusion of hydrogen to the detection electrode so that the deviation in λ point can be reduced to precisely control combustion of the internal combustion engine. On the other hand, the detection electrode side portion has a lower catalytic metal loading ratio for adsorbing unburned contents of the exhaust gas. Consequently, volume expansion of the catalytic metal can be suppressed to prevent the electrode-protecting layer from peeling off of the detection electrode.

DETAILED DESCRIPTION OF THE INVENTION

Figure 1:
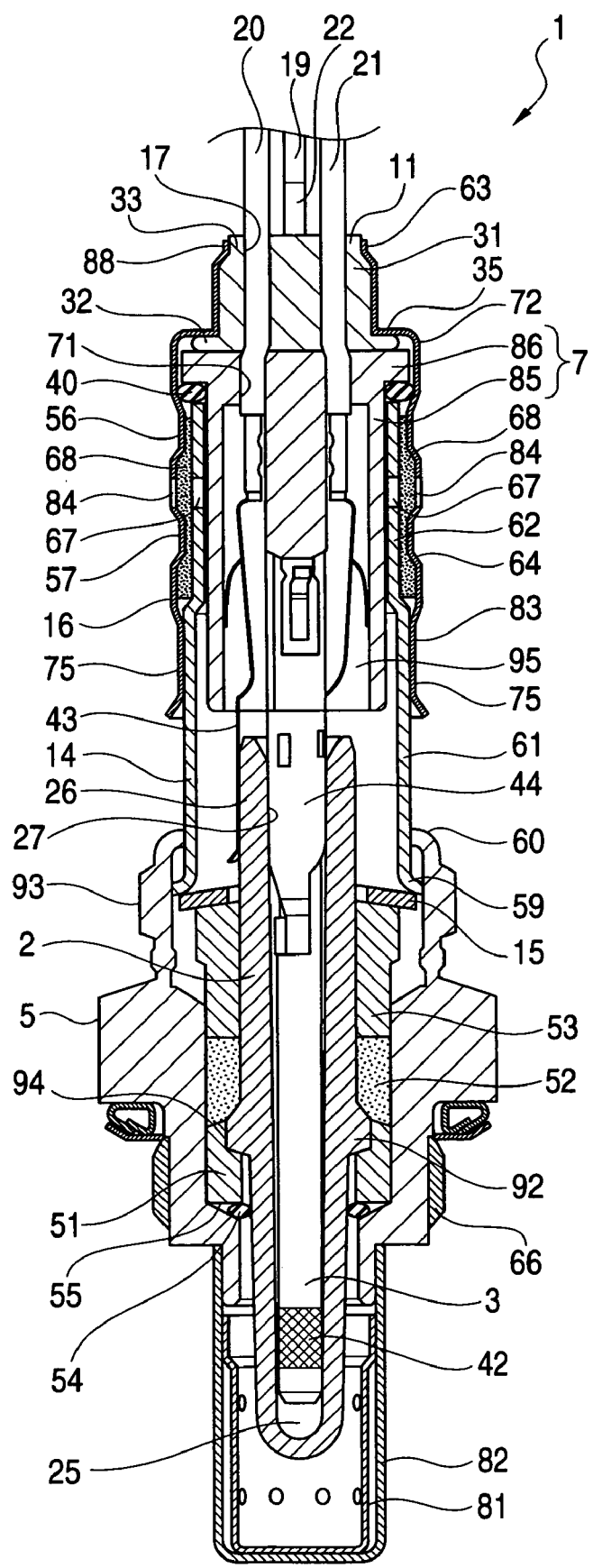
FIG. 1 is a sectional view of a gas sensor 1 of an embodiment of the invention.

A gas sensor according to an embodiment of the invention will next be described with reference to the accompanying drawings. However, the present invention should not be construed as being limited thereto. This embodiment describes a gas sensor (or an oxygen sensor), which is mounted in an exhaust pipe (i.e., on the downstream side of a catalyst) of an automobile for detecting the concentration of oxygen in the exhaust gas. FIG. 1 is a sectional view showing the entire configuration of the gas sensor 1 of this embodiment.

As shown in FIG. 1, the gas sensor 1 is provided with: a sensor element 2 having a bottomed cylindrical shape with a closed leading end portion; a ceramic heater 3 to be inserted into a bottomed hole 25 of the sensor element 2; and a metal shell 5 for holding the sensor element 2 in its inner side. In this embodiment, in the direction along the axis of the sensor element 2 shown in FIG. 1, the side (i.e., the closed side or the lower side of the drawing) toward the leading end to be exposed to the gas to be measured (i.e., the exhaust gas) is designated the "leading end side", and the side (i.e., the upper side of the drawing) toward the opposite side is designated the "trailing end side".

This sensor element 2 is equipped with: a solid electrolyte layer 28 composed mainly of partially stabilized zirconia containing dissolved yttria solid as a stabilizer and having oxygen ion conductivity; an inner electrode layer 27 formed of Pt or a Pt alloy in a porous shape which covers the substantially whole inner face of the bottomed hole 25 of the solid electrolyte layer 28; and an outer electrode layer 26 formed into a porous shape similar to the inner electrode layer 27 on the outer face of the solid electrolyte layer 28. The sensor element 2 is further equipped, at its substantially midway position in the axial direction, with an engaging flange portion 92 protruding radially outward. The ceramic heater 3 is formed into a rod shape and equipped with a heating portion 42 having a heating resistor therein. When this ceramic heater 3 is energized through heater lead wires 19 and 22 described below, the heating portion 42 generates heat. Thus, the ceramic heater 3 functions to heat and activate the sensor element 2.

The metal shell 5 is equipped with a threaded portion for mounting the gas sensor 1 in the mounting portion of the exhaust pipe, and a hexagonal portion 93 for applying a mounting tool when the gas sensor 1 is mounted in the mounting portion of the exhaust pipe. Moreover, the metal shell 5 is constructed to house therein: a support member 51 made of alumina for supporting the sensor element 2 on the leading end side; a filler member 52 made of talc powder filling the trailing end side of the support member 51; and a sleeve 53 made of alumina for pushing the filler member 52 from the trailing end side to the leading end side.

The metal shell 5 is equipped, on the inner circumference of its leading end side, with a fixture side step portion 54 protruding radially inward, and retains the support member 51 on that fixture side step portion 54 through a packing 55. The sensor element 2 is supported by the metal shell 5 such that the engaging flange portion 92 is supported on the support member 51 through a packing 94. The filler member 52 is arranged between the inner face of the metal shell on the trailing end side of the support member 51 and the outer face of the sensor element 2. On the trailing end side of the filler member 52, a sleeve 53 and an annular ring 15 are arranged so as to sequentially fit in a coaxial state.

An inner cylinder member 14 made of SUS304L is inserted into the trailing end side of the metal shell 5. This inner cylinder member 14 is fixed in the metal shell 5 by additionally fastening the trailing end portion 60 of the metal shell 5 toward the leading end while the diametrically open end portion (i.e., a leading end open end 59) abuts the annular ring 15. The gas sensor 1 is structured so that the filler member 52 is compressed and filled through the sleeve 53 by additionally fastening the fixture side trailing end portion 60 of the metal shell 5. As a result, the sensor element 2 is held gas-tight in the cylindrical metal shell 5.

The inner cylinder member 14 is formed: at its substantially middle position in the axial direction into a stepped portion 83; on the leading end side of the inner cylinder stepped portion 83 into a leading end side trunk portion 61; and on the trailing end side of the inner cylinder stepped portion 83 into a trailing end side trunk portion 62. The inner cylinder trailing end side trunk portion 62 is formed to have both an internal diameter and an external diameter smaller than those of the inner cylinder leading end side trunk portion 61 and to have an internal diameter slightly larger than the external diameter of a body portion 85 of a later-described separator 7. A plurality of air vent holes 67 are formed in the inner cylinder trailing end side trunk portion 62 at a predetermined interval along the circumferential direction.

An outer cylinder member 16 is formed into a cylindrical shape by deeply drawing a sheet material of SUS304L so as to have: on the leading end side, an outer cylinder trailing end side portion 63 having an opening leading from the outside to the inside; on the trailing end side, an outer cylinder leading end side portion 64 to be coaxially connected to the inner cylinder member 14 from the trailing end side; and an outer cylinder stepped portion 35 for connecting the outer cylinder trailing end side portion 63 and the outer cylinder leading end side portion 64. Here the outer cylinder trailing end side portion 63 is formed to have an additionally fastened portion 88 for fixing an elastic seal member 1 gas-tight.

Moreover, metallic double protectors 81 and 82 are welded to the outer circumference on the leading end side of the metal shell 5, which protectors cover the leading end portion protruding from the leading end of the metal shell 5 of the sensor element 2 and have a plurality of gas inlet holes.

On the outer side of the inner cylinder trailing end side trunk portion 62 of the inner cylinder member 14, moreover, a cylindrical filter 68 is arranged for preventing water from invading from the air vent holes 67. The filter 68 is structured as a water-repellent filter for blocking permeation of a liquid composed mainly of water but permitting permeation of a gas such as air. Filter 68 is made of a porous fiber structure of polytetrafluoroethylene (having a commercial name of GORETEX available from Japan Goretex, Inc.).

The outer cylinder leading end side portion 64 of the outer cylinder member 16 is formed into a shape which covers the inner cylinder member 14 (i.e., the inner cylinder trailing end side trunk portion 62) having the filter 68. A plurality of air vent holes 84 are formed in the outer cylinder leading end side portion 64 at positions corresponding to the filter 68 at a predetermined spacing along the circumferential direction.

The outer cylinder member 16 and the inner cylinder member 14 are additionally fastened by both a first portion 56, which is formed by additionally fastening at least a portion of the outer cylinder leading end side portion 64 of the outer cylinder member 16 on the trailing end side of the air vent holes 84 radially inward through the filter 68, and a second portion 57, which is formed by additional fastening at least a portion on the leading end side of the air vent holes 84 also radially inward through the filter 68. At this time, the filter 68 is held gas-tight between the outer cylinder member 16 and the inner cylinder member 14. Moreover, the outer cylinder leading end side portion 64 of the outer cylinder member 16 is arranged to overlap around the inner cylinder leading end side trunk portion 61, and at least a portion of the overlap portion is additionally fastened circumferentially inward to form an additionally fastened joint portion 75.

As a result, the ambient atmosphere as a reference gas is introduced through the air vent holes. 84, the filter 68 and the air vent holes 67 into the inner cylinder member 14 and into the bottomed hole 25 of the sensor element 2. On the other hand, water droplets cannot pass through the filter 68 and are prevented from invading to the inner side of the inner cylinder member 14.

In the elastic seal member 11 arranged on the trailing end inner side (i.e., the outer cylinder trailing end side portion 63) of the outer cylinder member 16, four lead wire inserting holes 17 are formed through the elastic seal member 11 from the leading end side to the trailing end side for inserting two element lead wires 20 and 21 electrically connected to the sensor element 2 and two heater lead wires 19 and 22 electrically connected to the ceramic heater 3.

In the separator 7 having its own leading end side inserted into and arranged in the inner cylinder trailing end side trunk portion 62 of the inner cylinder member 14, separator lead wire inserting holes 71 are formed through the separator 7 from the leading end side to the trailing end side for inserting the element lead wires 20 and 21 and the heater lead wires 19 and 22. In the separator 7, moreover, a bottomed holding hole 95 is formed in the axial direction, which is opened in the leading end face. The ceramic heater 3 is positioned in the axial direction with respect to the separator 7 by inserting the trailing end portion of the ceramic heater 3 into the holding hole 95 to bring its trailing end face into abutment against the bottom face of the holding hole 95.

Separator 7 is equipped with separator body portion 85 to be inserted into the trailing end of the inner cylinder member 14, and a separator flange 86 extended circumferentially outward from the trailing end portion of the separator body portion 85. Namely, the separator is arranged in the outer cylinder member 16 so that its body portion 85 is inserted into the inner cylinder member 14 and its flange portion 86 is supported on the trailing end face of the inner cylinder member 14 through an annular seal member 40 made of fluorine rubber.

The element lead wires 20 and 21 and the heater lead wires 19 and 22 are extracted through the separator lead wire inserting holes 71 of the separator 7 and through the lead wire inserting holes 17 of the elastic seal member 11 from the inside to the outside of the inner cylinder member 14 and the outer cylinder member 16. Here, the four lead wires 19, 20, 21 and 22 are connected with connectors (not shown) outside the sensor. Through the connectors, moreover, electric signals are inputted/outputted between an external device such as an ECU and the individual lead wires 19, 20, 21 and 22.

The individual lead wires 19, 20, 21 and 22 have a structure, in which a conductor is sheathed with an insulating skin made of a resin and in which the conductor is connected on its trailing end side with a connector terminal of a connector, although not shown in detail. Moreover, the leading end side of the conductor of the element lead wire 20 is additionally fastened to the trailing end portion of a terminal fixture 43 fitted on the outer face of the sensor element 2, and the leading end side of the conductor of the element lead wire 21 is additionally fastened to the leading end portion of a terminal future 44 press-fitted in the inner face of the sensor element 2. As a result, the element lead wire 20 is electrically connected with the outer electrode layer 26 of the sensor element 2, and the element lead wire 21 is electrically connected with the inner electrode layer 27. On the other hand, the leading end portions of the conductors of the heater lead wires 19 and 22 are individually connected with a pair of heater terminal fixtures joined to the heating resistor of the ceramic heater 3.

On the trailing end side of the separator 7, moreover, the elastic seal member 11 made of fluorine rubber having excellent heat resistance or the like is fixed in the outer cylinder member 16 by additionally fastening the outer cylinder member 16 to form the additionally fastened portion 38. This elastic seal member 11 is equipped with a body portion 31, and a seal member flanged portion 32 extending radially outward from a side circumference 72 of the leading end side of the body portion 31. Moreover, the four lead wire inserting holes 17 are formed in the axial direction through the body portion and a diametrically small portion 33.

Next, the sensor element 2 forming an essential portion of the invention is described in detail as follows.

Figure 2:
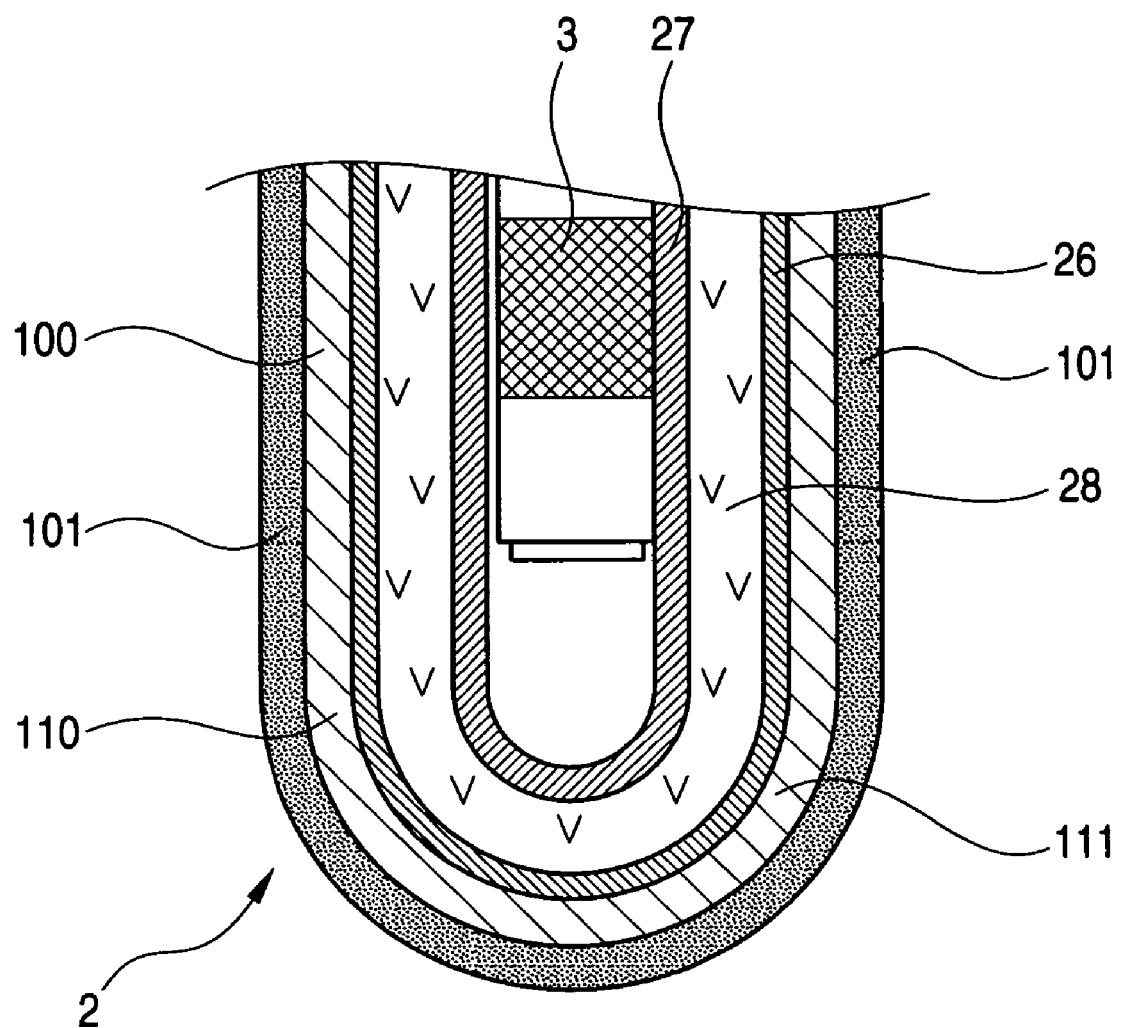
FIG. 2 is an enlarged sectional view of a sensor element 2 arranged in the gas sensor 1 of the embodiment.
Figure 3:
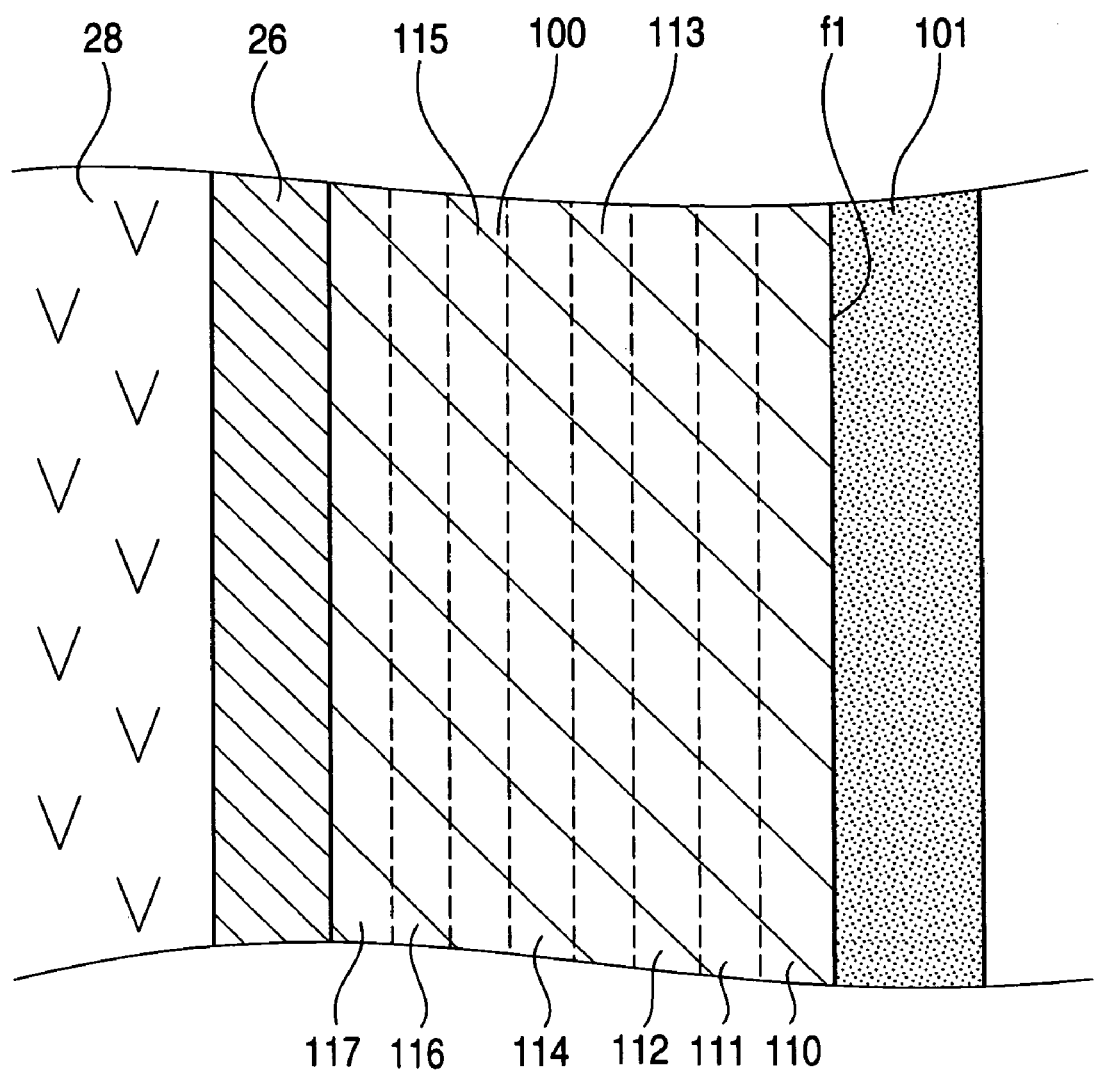
FIG. 3 is an enlarged view illustrating an outermost surface side portion 110 and an outer electrode side portion 117 in the sensor element of FIG. 2.

As shown in FIG. 2 and FIG. 3, the sensor element 2 is further equipped with a porous electrode-protecting layer 100 for sheathing the outer electrode layer 26.

This electrode-protecting layer 100 is made of refractory ceramics such as alumina-magnesia-spinel and carries catalytic metal. This electrode-protecting layer 100 has a thickness of 200 μm and a porosity of 40%. The carried catalytic metal is made of platinum having an average particle diameter of 0.01 to 5 μm. Moreover, the catalytic metal is carried (or loaded) in an amount of 60 μg by the electrode-protecting layer 100.

The electrode-protecting layer 100 thus carries the catalytic metal so that the electrode-protecting layer 100 can be exposed directly to the exhaust gas without providing another catalyst layer. Specifically, the catalytic metal carried by the electrode-protecting layer 100 can suppress diffusion of hydrogen to the outer electrode layer 26 and can reduce the deviation of λ point to thereby provide the gas sensor 1 which can precisely control the combustion of an internal combustion.

Moreover, the electrode-protecting layer 100 is equipped, from its surface f1 to a thickness of 25 μm, with an outermost surface side portion 110, having a catalytic metal loading ratio of 0.012% by weight. Wrth the electrode-protecting layer 100 loaded with catalytic metal at a ratio of 0.01% by weight or more, hydrogen in the exhaust gas can sufficiently react to suppress diffusion of hydrogen to the outer electrode layer 26 and reduce deviation in λ point, to thereby control combustion of the internal combustion engine.

The electrode-protecting layer 100 is further equipped, to a thickness of 25 μm from the outer electrode layer 26, with an outer electrode layer side portion 117 having a catalytic metal loading ratio of 0.0015% by weight. Thus, the electrode-protecting layer 100 is equipped with the outer electrode layer side portion 117 thus loaded with catalytic metal at a ratio of 0.005% by weight or less (not including 0) so that the amount of catalytic metal adsorbing unburned contents of the exhaust gas can be reduced. This in turn suppresses volume expansion of the catalytic metal, and prevents the electrode-protecting layer 100 from peeling off of the outer electrode layer 26.

Moreover, there is a gradient in the loading ratio of the catalytic metal in the thickness direction of the electrode-protecting layer 100, which is lowest at the innermost electrode layer side portions 117 of the electrode-protecting layer 100, and which progressively increases at intermediate portions 116, 115, 114, 113, 112 and 111 and reaches the highest loading ratio at the outermost surface side portion 110. Specifically, the electrode-protecting layer 100 having a thickness of 200 μm is divided by a thickness of 25 μM from the surface side into eight portions 110, 111, 112, 113, 114, 115, 116 and 117. The loading ratios of the catalytic metal are next compared among the individual portions. The loading of the catalytic metal in a portion closer to the outer electrode is less than that in a portion closer to the surface of the electrode-protecting layer. As a result, stress caused by volume expansion of the catalytic metal in the electrode-protecting layer 100 becomes gradually lower from the side of the surface f1 of the electrode-protecting layer 100 to the side of the outer electrode layer 26. As a result, close contact between the electrode-protecting layer 100 and the outer electrode layer 26 can be maintained to suppress peeling of the electrode-protecting layer 100 from the outer electrode layer 26.

As shown in FIG. 2, moreover, on the outer face of the electrode-protecting layer 100 a porous poison preventing layer 101 is formed, which covers the electrode-protecting layer 100. This poison preventing layer 101 prevents the catalytic metal in the electrode-protecting layer 100 from being damaged by poisonous substances such as lead, phosphor or silicon in the exhaust gas.

This poison preventing layer 101 is made of a ceramic body composed of titania and a ceramic other than titania Titania is excellent in adsorbing poisonous substances, and the poison preventing layer 101 containing the titania can effectively react with poisonous substances such as phosphor in the exhaust gas to thereby prevent the catalytic metal in the outer electrode layer 26 and the electrode-protecting layer 100 from becoming poisoned. On the other hand, preferable ceramic powder other than the titania is exemplified by ceramic powder resistant to thermal shrinkage, such as spinel or mullite. By using such a ceramic material, durability of the poison preventing layer 101 can be improved by preventing the poison preventing layer 101 from peeling off of the electrode-protecting layer 100 due to thermal shrinkage.

Moreover, a combination of materials for the poison preventing layer 101 is preferably made comprising primary particles of the titania powder having a peak particle size of 0.003 to 0.5 μm and primary particles of ceramic powder other than titania having a peak particle size of 15 to 65 μm By this combination, the poison preventing layer 101 can bear a proper porosity to secure sufficient air permeability and sufficient adsorption of poisonous substances.

Moreover, the poison preventing layer 101 preferably has a thickness of 50 to 300 μm. A thickness less than 50 μm has difficulty in sufficiently adsorbing poisonous substances. On the other band, in a thickness greater than 300 μm, the poison preventing layer 101 tends to peel off of the electrode-protecting layer 100.

The outer electrode layer 26 in this embodiment corresponds to the "detection electrode"; and the inner electrode layer 27 in this embodiment corresponds to the "reference electrode".

Next, a method for manufacturing the gas sensor 1 of this embodiment is described in detail as follows. First, a solid electrolyte layer 28 is obtained by adding 5 mol % yttria to zirconia and granulating the mixture, forming the granulate into a bottomed cylinder shape having a closed leading end portion, as shown in FIG. 1, and firing the bottomed cylinder in an electric furnace at a temperature of 1,400 to 1,600° C. Next, the outer electrode layer 26 made of platinum is formed on the outer circumference of the solid electrolyte layer 28 by evaporation, chemical plating or the like. On the other hand, the inner electrode layer 27 is also formed on the inner side face of the solid electrolyte layer 28 by evaporation, chemical plating or the like.

Next, a refractory ceramic such as alumina-magnesia-spinel is plasma-spray coated on the surface of the outer electrode layer 26 to form a porous body of the electrode-protecting layer 100. Then, the porous body of the electrode-protecting layer 100 is dipped in an aqueous solution of $H_2PtCl_6$, and a vacuum state is established to carry platinum as a catalytic metal in the electrode-protecting layer 100. The porous body of the electrode-protecting layer 100 is dipped in the aqueous solution of $H_2PtCl_6$ for 5 minutes to 20 minutes. After this, the porous body is dried and heated in an electric furnace at 200 to 800° C. for 5 minutes to 30 minutes.

Since the catalytic metal is carried in the electrode-protecting layer 100, the electrode-protecting layer 100 itself can be exposed directly to exhaust gas. Therefore, it is possible to provide the gas sensor 1, which is able to suppress diffusion of hydrogen to the outer electrode layer 26 by the catalytic metal carried in the electrode-protecting layer 100, to reduce deviation in $\lambda$ point and to precisely control combustion of the internal combustion engine.

In the electrode-protecting layer 100 thus formed by the aforementioned method, moreover, the loading ratio of the catalytic metal of the electrode-protecting layer 100 is decreased in the thickness direction from the outermost surface portion 110 of the electrode-protecting layer 100 to the outer electrode layer side portion 117 of the electrode-protecting layer 100. By decreasing the loading ratio of the catalytic metal toward the side of the outer electrode layer 26 of the electrode-protecting layer 100 relative to the side of the surface f1 of the electrode-protecting layer 100, stress due to volume expansion of the catalytic metal in the electrode-protecting layer 100 can be dually reduced from the surface side of the electrode-protecting layer 100 to the side of the outer electrode layer 26 As a result, close contact between the electrode-protecting layer 100 and the outer electrode layer 26 can be maintained to suppress peeling of the electrode-protecting layer 100 from the outer electrode layer 26.

Next, a slurry is made of predetermined amounts of titania powder, ceramic powder other than titania, alumina sol and nylon pebbles, which components are mixed in a pot mill to adjust the slurry. Taking this slurry as 100% by weight, the titania powder and the ceramic powder other than titania are 70% by weight, and the alumina sol is 7% by weight. By dipping the solid electrolyte layer 28 having the electrode-protecting layer 100 in the slurry, a coating film on the surface of the electrode-protecting layer 100 is formed. Then, by drying the electrode-protecting layer 100 at 600 to 730° C., a poison preventing layer 101 is formed. Thus, the sensor element 2 according to his embodiment is obtained.

Next, a method for manufacturing the gas sensor by assembling it with the sensor element 2 above is described as follows. First, the element lead wires 20 and 21 are joined to the terminal fixtures 43 and 44, respectively, and the heater lead wires 19 and 22 are joined to the heater terminal fixtures of the ceramic heater 3. With the ceramic heater 3 being positioned in the terminal fixture 44, moreover, the individual lead wires 19, 20, 21 and 22 are inserted into the individual separator lead wire inserting holes 71 of the separator 7. With the individual lead wires 19, 20, 21 and 22 being inserted into the lead wire inserting holes 17 of the elastic seal member 11, the leading end face of the elastic seal member 11 is then moved to abut the trailing end face of the separator 7. Thus, the sensor upper portion intermediate is prepared. Here, the annular seal member 40 is mounted in advance on the outer circumference of the separator body portion 85.

Figure 4:
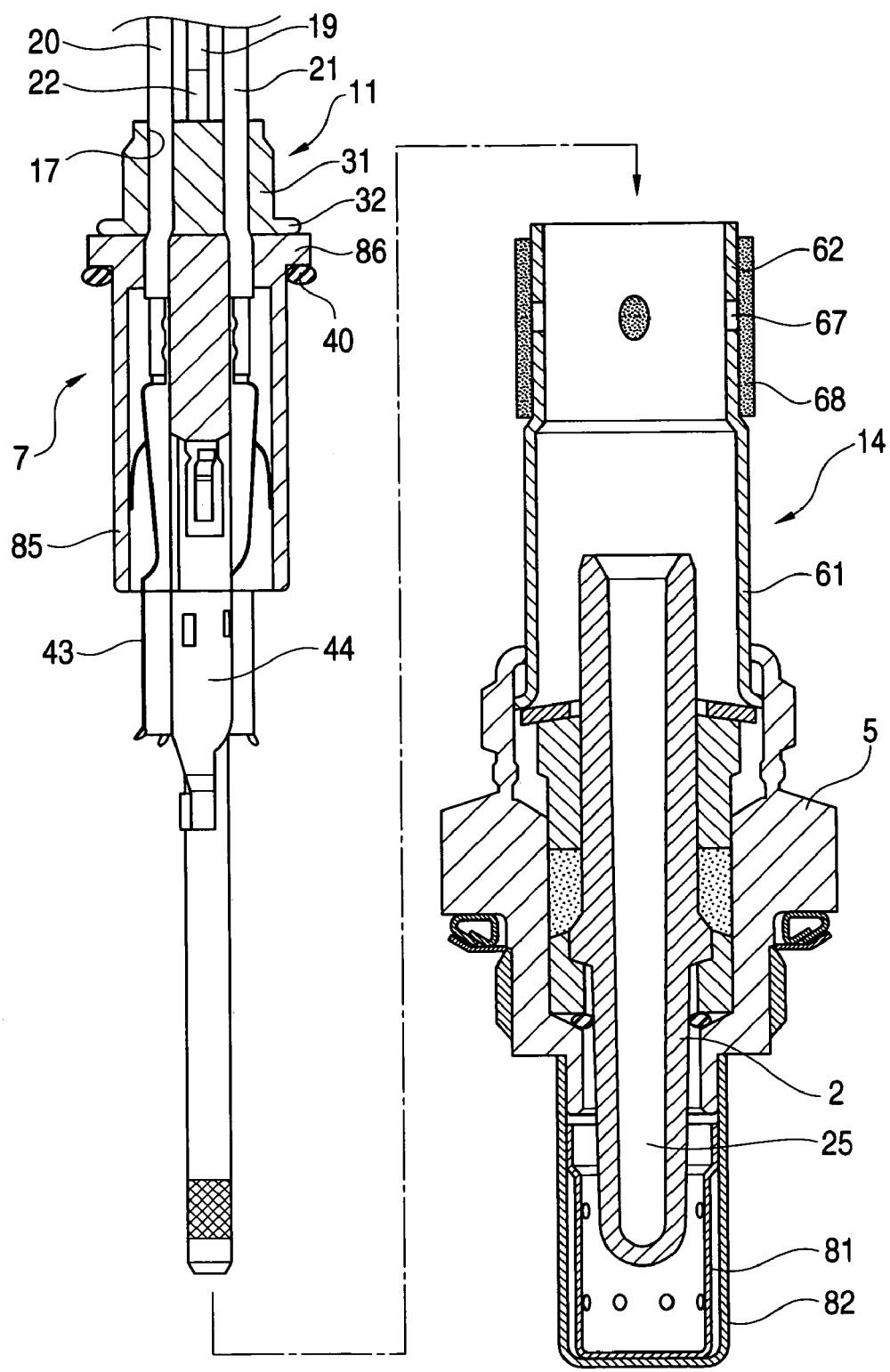
FIG. 4 is an assembly diagram of the gas sensor 1 of the embodiment.

Next, the sensor lower portion intermediate is prepared, in which the sensor element 2 is held in the metal shell 5 and in which the leading end side of the inner cylinder member 14 is connected to the trailing end side of the metal shell 5 while the protectors 81 and 82 are welded to the leading end side of the metal shell 5, as shown in FIG. 4. Here, the cylindrical filter 68 is set around the inner cylinder trailing end side trunk portion 62 of the inner cylinder member 14. Then, the body portion 85 of the separator of the sensor upper portion intermediate is positioned in the trailing end side trunk portion 62 of the inner cylinder member 14 of the sensor lower portion intermediate. As a result, the terminal fixture 44 is inserted together with the ceramic beater 3 into the bottomed hole 25 of the sensor element 2 so that it is connected to the inner electrode layer 27. The terminal fixture 43 is fitted on the outer face of the sensor element 2 so that it is connected to the outer electrode layer 26.

Then, the outer cylinder member 16 is moved while inserting the individual lead wires 19, 20, 21 and 22 into the outer cylinder member 16, from the trailing end side of the elastic seal member 11 so far as to overlap the outer side of the leading end side trunk portion 62 of the inner cylinder member 14. While the outer cylinder stepped portion 35 is pushed toward the leading end side in the axial direction, the overlapping portion of the outer cylinder member 16 and the inner cylinder leading end side trunk portion 62 is then additionally fastened radially inward to form the additionally fastened joint portion 75 to thereby fix the outer cylinder member 16 and the inner cylinder member 14. Here, the additional fastening is performed equally in all directions.

Figure 5:
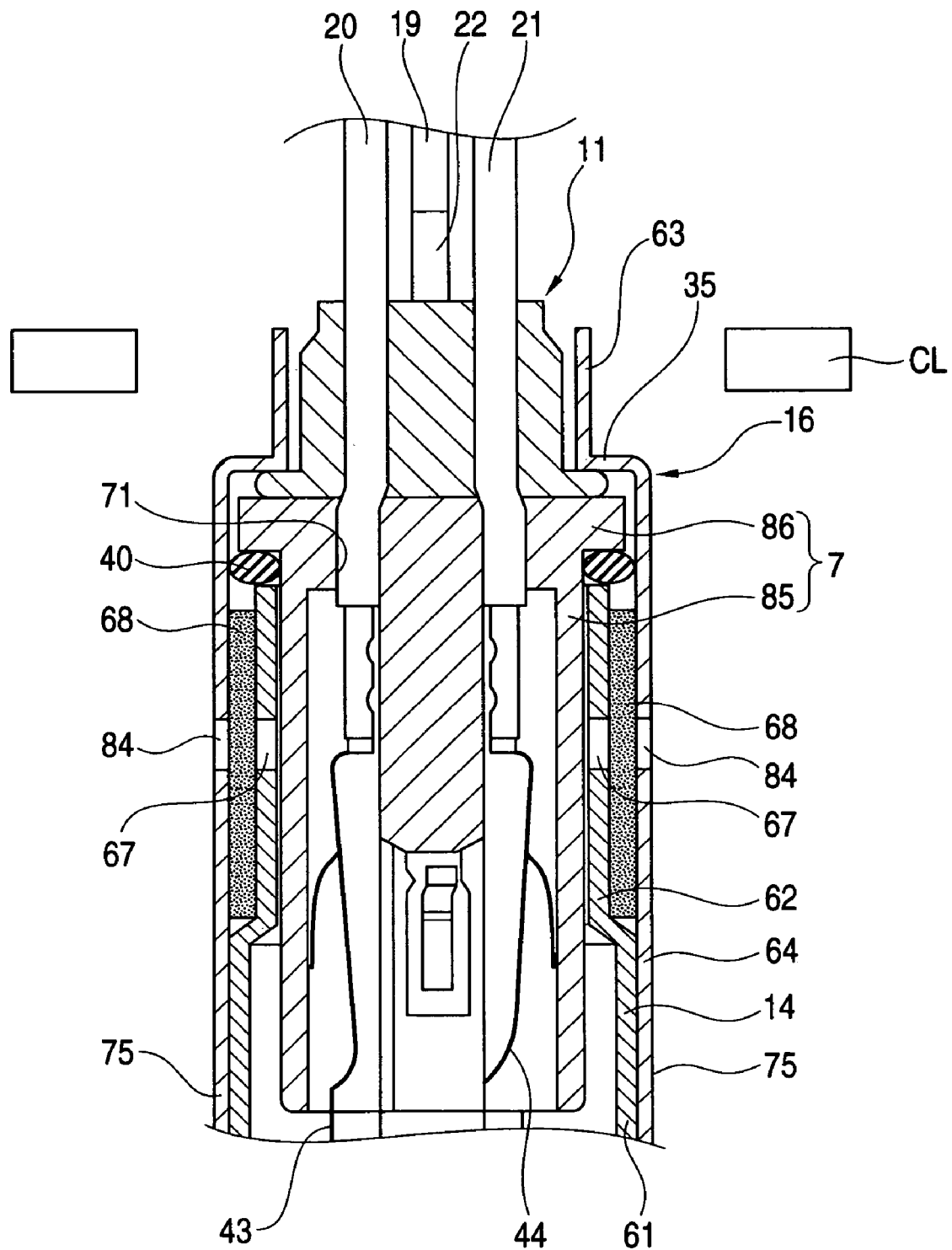
FIG. 5 is an assembly diagram showing further details of the gas sensor 1 of the embodiment.

Next, the outer cylinder member 16 (or its trailing end side portion 63) is additionally fastened by a caulking tool CL, at its portion located on the circumferentially outer side of the elastic seal member 11 (i.e., on the trailing end portion of the outer cylinder trailing end side portion 63), radially inward to form the additionally fastened portion 88, as shown in FIG. 5, to thereby compress and deform the elastic seal member 11. As a result, the elastic seal member 11 is fixed gas-tight in the outer cylinder member 16. This additional fastening is also performed equally in all directions. Then, the gas sensor 1 is completed by forming the first additionally fastened portion 56 and the second additionally fastened portion 57 with respect to the outer cylinder member 16 and the inner cylinder member 14 fixed by the additionally fastened joint portion 75.

EXAMPLES

The following various experiments were done to confirm the effects of the invention.

The various test pieces of the sensor element 2 having the shape shown in FIG. 2 were prepared in the following manner. First, zirconia having 5 mol % of yttria added thereto was granulated and formed into a bottomed cylinder shape. This bottomed cylinder was fired at 1,300° C. for 2 hours to prepare the solid electrolyte layer 28. Next, the solid electrolyte layer 28 was plated with Pt on its outer circumference and its inner circumference to form the outer electrode layer 26 and the inner electrode layer 27. Then, the outer electrode layer 26 was plasma-spray coated on its surface with alumina-magnesia-spinel to form the porous body of the electrode-protecting layer 100 having a thickness of 200 μm.

In Example 1, the porous body of the electrode-protecting layer 100 was then dipped in vacuum in a $H_2PtCl_6$ solution for 10 minutes. The $H_2PtCl_6$ solution contained 0.3 g/l of Pt. In Comparison 1, on the other hand, the porous body of the electrode-protecting layer 100 was dipped in vacuum in a $H_2PtCl_6$ solution for 10 minutes. This $H_2PtCl_6$ solution contained 3 g/l of Pt In short, Example 1 and Comparison 1 differed with respect to the Pt contents of the aqueous solution. Next, both Example 1 and Comparison 1 were dried and then heated in an electric furnace at 700° C. for 20 minutes. The porous body of the electrode-protecting layer 100 in Comparison 2 was not dipped in the aqueous solution. Twelve samples were individually prepared for each of Example 1, Comparison 1 and Comparison 2.

In the samples of Example 1, Comparison 1 and Comparison 2, moreover, the loading ratios of catalytic metal in the outermost surface side portion 110 and the outer side electrode side portion 117 were examined. In this regard, ten portions of about 2.5 μm were scraped off at the outermost surface side portion 110 in the thickness direction from the surface f1 of the electrode-protecting layer 100. Then, the scraped off outermost surface side portion 110 was weighed. Next, the scraped off outermost surface side portion 110 was dissolved in aqua regia to elute the catalytic metal, and its weight was measured by an ICP luminescence method. The weight % of the catalytic metal to the outermost surface side portion 110 was calculated. The same was repeated for outer side electrode side portion 117 in a thickness of about 25 μm. The results are shown in Table 1. Ten samples portions at each of layers 110 and 117 were individually evaluated to enhance measurement precision. The data in Table 1 represents average values.

TABLE 1

| | outermost surface side portion 110 (% by weight) | outer side electrode side portion 117 (% by weight) | Hydrogen Cleanability | Peelability |
|---|---|---|---|---|
| Ex. 1 | 0.012 | 0.0015 | o | o |
| Comp. 1 | 0.12 | 0.015 | o | x |
| Comp. 2 | 0 | 0 | x | o |

Figure 6:
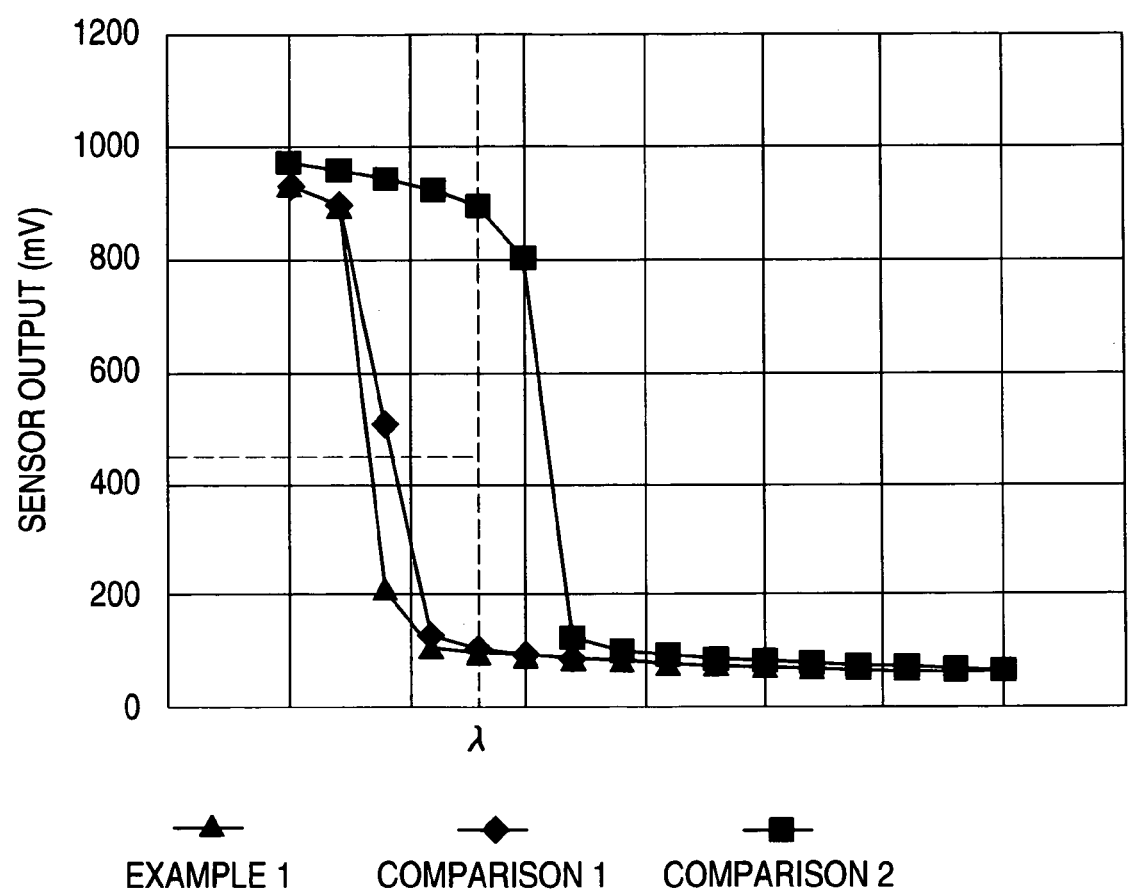
FIG. 6 presents an evaluation result of hydrogen cleaning ability of the Example of the invention.

Next, the hydrogen cleanability of the respective samples was evaluated. Specifically, the poison preventing layer 101 was formed on the sensor elements 2 of Example 1, Comparison 1 and Comparison 2. Moreover, the gas sensor 1 was fabricated by assembling the sensor element 2 with the metal shell 5 and the outer cylinder member 16 by the aforementioned manufacturing method. Then, the gas sensor f was assembled to expose the detecting portion (or the leading end side) of the sensor element 2 to the inside of an exhaust pipe, and the heater 3 was heated to raise the temperature of the detecting portion of the sensor element to 600° C. Next, a gas at a temperature of 450° C. to be measured was supplied at a total flow rate of 40 l/min from upstream to downstream of the exhaust pipe The gas to be measured was prepared by fixing the concentration of hydrogen at 0.35 vol %, by changing the flow rate of oxygen from low to high and by adjusting the remainder with nitrogen so that the total flow rate was constant. Then, the electromotive force generated by the gas sensor 1 was measured. The results are tabulated in FIG. 6 and Table 1. In Table 1, the symbol o indicates that the sensor output value abruptly varied at the λ point or below for a sensor output of 450 mV, and the symbol x indicates that the sensor output value abruptly varied above the λ point for a sensor output value of 450 mV.

Moreover, peel resistance of the electrode-protecting layer 100 on the sensor elements of Example 1, Comparison 1 and Comparison 2 was also evaluated. Specifically, the poison preventing layer 101 was formed on the sensor elements 2 of Example 1, Comparison 1 and Comparison 2. This gas sensor element 2 was heated to 900° C. for 1 minute, then left cold for 1 minute and then air-cooled for 1 minute to 100° C. After 2,000 cycles, the electrode-protecting layer 100 was observed. The symbol x indicates that the electrode-protecting layer 100 of the sensor element peeled off and the symbol o indicates that the electrode-protecting layer 100 of the sensor element 2 did not peel off. The results are tabulated in Table 1.

The above-noted results show that Example 1 can provide both excellent hydrogen cleaning ability and peel resistance.

The invention has been described in connection with the above embodiment. However, the invention should not be construed as being limited thereto, and encompasses various design changes within a range capable of achieving the object of the invention.

For example, the above embodiment has been exemplified by an oxygen-concentration electromotive force type sensor. However, the invention is not be limited thereto, and can also be applied to a threshold current type sensor.

This application is based on Japanese Patent application JP 2004-214907, filed Jul. 22, 2004, and Japanese Patent application JP 2005-193184, filed Jun. 30, 2005, the entire contents of which are hereby incorporated by reference, the same as if set forth at length.

What is claimed:

1. A gas sensor comprising a gas sensor element which includes:
   a reference electrode for contacting a reference gas;
   a solid electrolyte layer having oxygen ion conductivity;
   a detection electrode for contacting a gas to be measured; and
   an electrode-protecting layer covering said detection electrode, the electrode-protecting layer comprising a porous body carrying catalytic metal,
   wherein said electrode-protecting layer includes:
   a detection electrode side portion having a catalytic metal loading ratio of more than 0% by weight and not more than 0.005% by weight; and
   a surface side portion provided closer to the outer surface of said electrode-protecting layer than said detection electrode side portion, said surface side portion having a catalytic metal loading ratio of 0.01% by weight or more,
   wherein the catalytic metal loading ratio of said electrode-protecting layer decreases in a thickness direction from said outer surface side of said electrode-protecting layer to the detection electrode side of said electrode-protecting layer,
   wherein said electrode-protecting layer has a thickness of from 150 to 500 μm,
   wherein the detection electrode side portion is a portion of the electrode-protecting layer which has a 25 μm thickness from the detection electrode, and the surface side portion is a portion of the electrode-protecting layer which has a 25 μm thickness from the outer surface, and wherein the catalytic metal loading ratios of the electrode-protecting layer have consecutive 25 μm thickness ranges that progressively decrease from the outer surface side to the detection electrode side in the thickness direction.

2. The gas sensor as claimed in claim 1, wherein said porous body of said electrode-protecting layer contains at least one of alumina, alumina-magnesia-spinel and zirconia.

3. The gas sensor as claimed in claim 1, wherein said catalytic metal comprises at least one of Pt, Pd, Rh and Ru.

4. The gas sensor as claimed in claim 1, wherein said gas sensor element further includes a porous poison preventing layer covering said electrode-protecting layer for preventing said catalytic metal from becoming poisoned.

5. The gas sensor as claimed in claim 4, wherein said poison preventing layer contains titania and ceramic other than titania.

6. The gas sensor as claimed in claim 5, wherein said poison preventing layer is formed from titania powder and ceramic powder other than said titania powder, wherein said titania powder contains primary particles having a peak particle size distribution of 1 μm or lower, and said ceramic powder other than titania contains primary particles having a peak particle size distribution of 10 μm or higher.

7. A method for manufacturing a gas sensor comprising a gas sensor element including a reference electrode for contacting a reference gas, a solid electrolyte layer having oxygen ion conductivity, a detection electrode for contacting a gas to be measured, and an electrode-protecting layer provided covering said detection electrode, the electrode-protecting layer comprising a porous body carrying catalytic metal, said method comprising:

spray coating a porous body on said detection electrode;

impregnating said porous body with catalytic metal from its outer surface; and heating the porous body impregnated with said catalytic metal to form said electrode-protecting layer, wherein said electrode-protecting layer includes:

a detection electrode side portion having a catalytic metal loading ratio of more than 0% by weight and not more than 0.005% by weight; and a surface side portion provided closer to the outer surface of said electrode-protecting layer than said detection electrode side portion, said surface side portion having a catalytic metal loading ratio of 0.01% by weight or more, wherein the catalytic metal loading ratio of said electrode-protecting layer decreases in a thickness direction from said outer surface side of said electrode-protecting layer to the detection electrode side of said electrode-protecting layer, wherein said electrode-protecting layer has a thickness of from 150 to 500 μm, wherein the detection electrode side portion is a portion of the electrode-protecting layer which has a 25 μm thickness from the detection electrode, and the surface side portion is a portion of the electrode-protecting layer which has a 25 μm thickness from the outer surface, and wherein the catalytic metal loading ratios of the electrode-protecting layer have consecutive 25 μm thickness ranges that progressively decrease from the outer surface side to the detection electrode side in the thickness direction.

* * * * *